United States Patent [19]
Holzer et al.

[11] Patent Number: 5,550,374
[45] Date of Patent: Aug. 27, 1996

[54] METHODS AND APPARATUS FOR DETERMINING INTERSTITIAL OXYGEN CONTENT OF RELATIVELY LARGE DIAMETER SILICON CRYSTALS BY INFRARED SPECTROSCOPY

[75] Inventors: Joseph C. Holzer, Manchester; Harold W. Korb, Ballwin, both of Mo.; Klaus Drescher, Bochum, Germany

[73] Assignee: MEMC Electronic Materials, Inc., St. Peters, Mo.

[21] Appl. No.: 241,972

[22] Filed: May 12, 1994

[51] Int. Cl.$^6$ .................................................. G01N 21/35
[52] U.S. Cl. ............................. 250/339.07; 250/339.12; 250/341.4
[58] Field of Search .................... 250/339.07, 339.08, 250/339.12, 341.4

[56] References Cited

U.S. PATENT DOCUMENTS

| | | | |
|---|---|---|---|
| 4,436,577 | 3/1984 | Frederick et al. | 156/617 SP |
| 4,590,574 | 5/1986 | Edmonds et al. | 250/339.08 X |
| 4,862,000 | 8/1989 | Kubota et al. | 250/339.08 X |
| 4,956,153 | 9/1990 | Yamagishi et al. | 422/249 |
| 5,066,599 | 11/1991 | Kaneta et al. | 250/341.4 X |
| 5,248,378 | 9/1993 | Oda et al. | 156/617 |
| 5,386,118 | 1/1995 | Kitagawara et al. | 250/340 X |

FOREIGN PATENT DOCUMENTS

| | | | |
|---|---|---|---|
| 62-130341 | 6/1987 | Japan | 250/339.12 |
| WO95/07546 | 3/1995 | WIPO | |

OTHER PUBLICATIONS

Technical Description, "Device for Oxygen Measurements in Silicon Single Crystals", JV MANT Belarus, 1994, pp. 1–45.

"Standard Practices for Determination of the Concentration of Impurities in Single Crystal Semiconductor Materials by Infrared Absorption Spectroscopy", vol. 10.05, 1993, pp. 163–169.

B. Pajot, "Quantitative Spectroscopy of Interstitial Oxygen in Silicon", 1985, pp. 3034–3037.

B. Pajot & B. Cales, "Infrared Spectroscopy of Interstitial Oxygen in Silicon", 1966, pp. 39–45.

"Standard Test Method for Interstitial Atomic Oxygen Content of Silicon by Infrared Absorption" vol. 10.05, 1993, pp. 561–563.

K. Krishnam, P. J. Stout, Masaharu Watanabe, "Characterization of Semiconductor Silicon Using Fourier Transform Infrared Spectrometry", 1990, pp. 285–307.

A. S. Oates, Michael Stavola, "Infrared Spectrum of Oxygen in Silicon", 1987, pp. 3114–3116.

"Spektrometer für die Automatische Sauerstoffverteilungsbestimmung in Siliziumblöcken", No Date Available.

MAMT, "Oxygen-Spectrometer", No Data Available.

Daedal, Maual & Motorized "Positioning Systems", 1993 1993, pp. C34–C39.

*Primary Examiner*—Carolyn E. Fields
*Assistant Examiner*—Edward J. Glick
*Attorney, Agent, or Firm*—Senniger, Powers, Leavitt & Roedel

[57] ABSTRACT

Nondestructive methods and apparatus for determining a concentration of interstitial oxygen in a generally cylindrical body of crystalline silicon. The invention transmits an infrared (IR) beam through the body generally transverse to a longitudinal axis of the body and measures the absorption coefficient of an interstitial oxygen absorption band at a wavenumber $W_p$ of approximately 1720 cm$^{-1}$. Further, the invention determines the concentration of interstitial oxygen in the body as a function of the measured absorption coefficient.

12 Claims, 6 Drawing Sheets

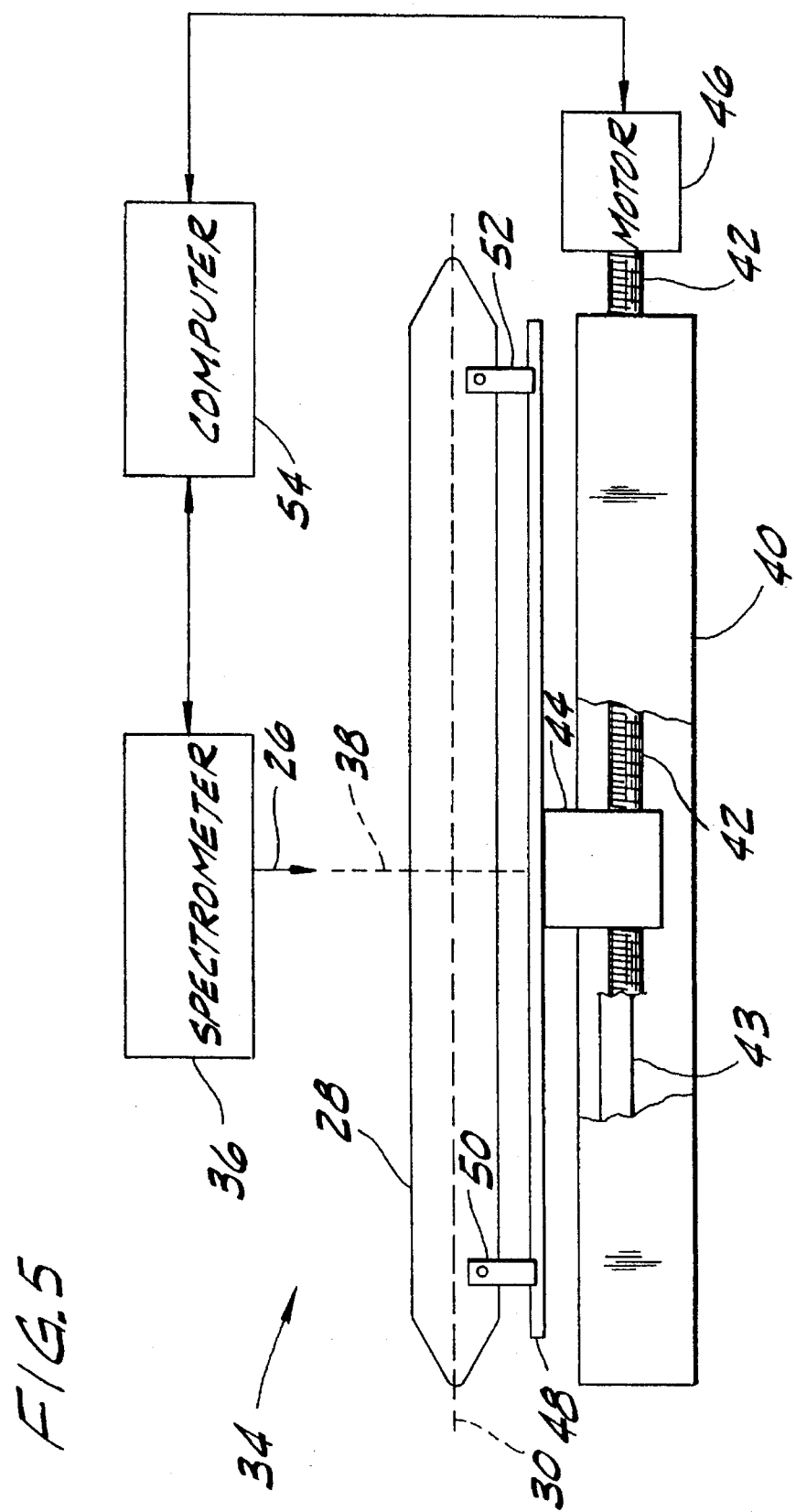

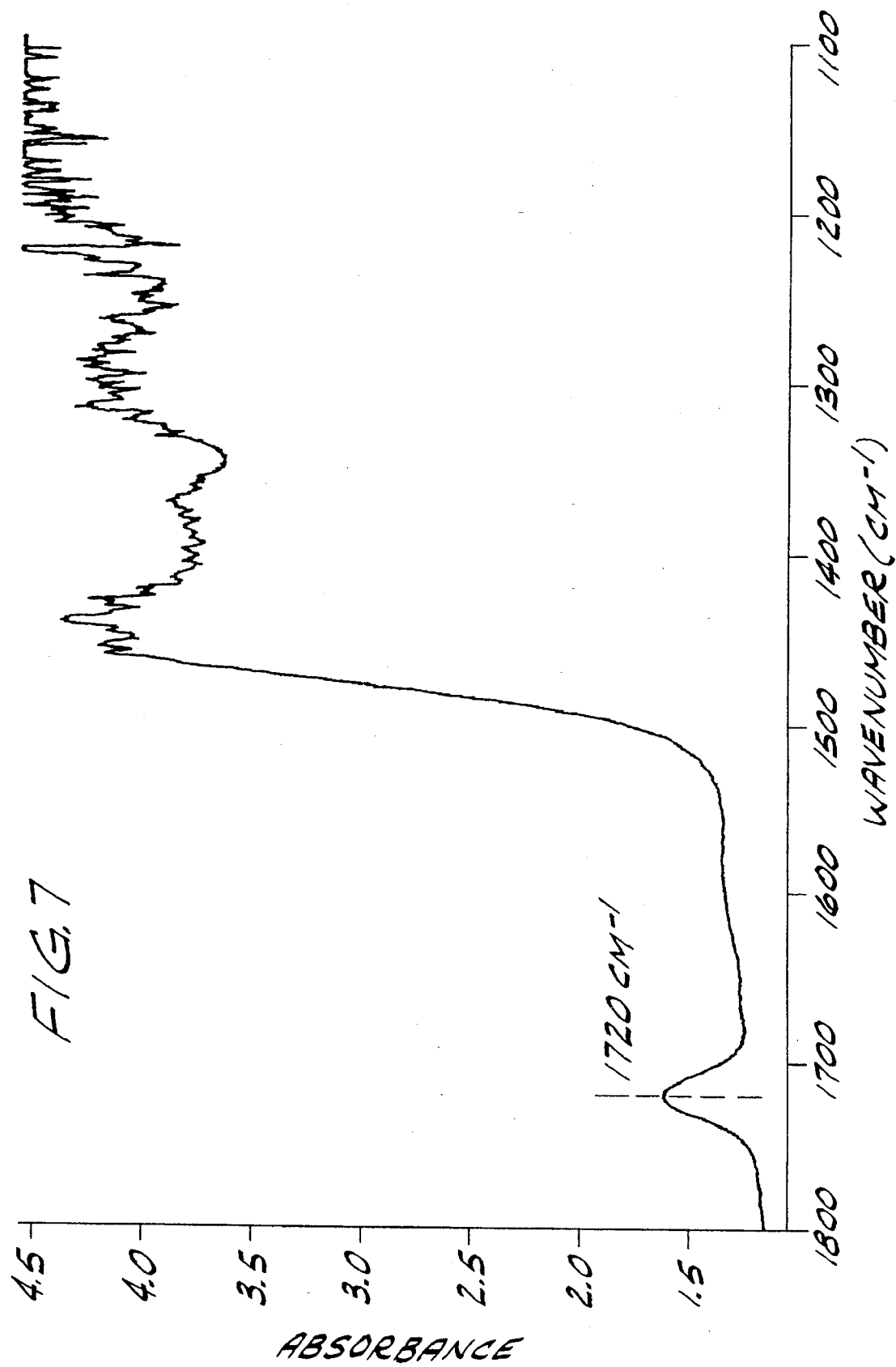

METHODS AND APPARATUS FOR DETERMINING INTERSTITIAL OXYGEN CONTENT OF RELATIVELY LARGE DIAMETER SILICON CRYSTALS BY INFRARED SPECTROSCOPY

BACKGROUND OF THE INVENTION

This invention relates to improved methods and apparatus for determining concentrations of interstitial oxygen in crystalline silicon by infrared (IR) spectroscopy.

Generally, oxygen atoms and other impurities contaminate crystalline silicon. As an example, crystals grown by the Czochralski process may have an oxygen concentration as high as 30 parts per million atomic (ppma) (ASTM F 1188-93). in the Czochralski process, oxygen from quartz crucibles used to hold a melt from which silicon crystals are grown will dissolve into the silicon melt. Also, oxygen in the ambient atmosphere surrounding the melt can likewise dissolve in the silicon melt. The oxygen dissolved in the melt is then incorporated into the crystal at the liquid-solid interface. Oxygen atoms typically occupy interstitial sites in the silicon unit cell and form two strong Si—O bonds with the nearest-neighbor silicon atoms.

The electrical performance of integrated circuit (IC) devices depends in part on the material properties of the silicon used in fabrication of the finished IC devices. The presence of oxygen in the silicon lattice is either beneficial or detrimental to device performance depending on its concentration. Therefore, improved silicon device manufacturing requires accurate measurement and control of the amount of dissolved oxygen in silicon crystals.

The semiconductor industry widely uses infrared (IR) spectroscopy for characterizing silicon based on the content of interstitial oxygen in crystals. Generally, silicon is transparent to IR radiation and the IR transmission or absorption spectrum exhibits several absorption bands caused by the vibrations of impurities in the silicon lattice. The standard method for measuring the interstitial oxygen content of silicon by Fourier transform infrared (FTIR) spectroscopy is described in the American Society for Testing and Materials (ASTM) Designation F 1188-93 entitled "Standard Test Method for Interstitial Atomic Oxygen Content of Silicon by Infrared Absorption". However, this method is limited to relatively thin samples of the crystal and require relatively expensive, inefficient and time-consuming steps for preparing the samples.

SUMMARY OF THE INVENTION

Among the objects and features of the present invention may be noted the provision of an improved method for performing spectroscopy which permits measuring an IR absorption or transmission spectrum for a relatively thick body of crystalline silicon without cutting or sawing the crystal; the provision of such a method which permits measuring an IR absorption or transmission spectrum for crystalline silicon without grinding or polishing the surface of the crystal; the provision of such a method which decreases the time needed to prepare a crystal for spectroscopy; the provision of such a method which reduces crystal waste; the provision of such a method which permits quickly adjusting the crystal growing process for controlling interstitial oxygen concentration in subsequently grown silicon crystals; and the provision of such a method which can be carried out efficiently and relatively inexpensively.

Further among the objects and features of the present invention may be noted the provision of a system operating according to the method of this invention which permits easily measuring oxygen distribution throughout a crystal; the provision of such a system which permits smoothly positioning and repositioning a crystal with respect to a spectrometer; and the provision of such a system which is economically feasible and commercially practical.

Briefly described, a method according to the present invention includes the step of transmitting an IR beam through a generally cylindrical body of crystalline silicon generally transverse to a longitudinal axis of the body. The method further includes the steps of measuring the absorption coefficient of an interstitial oxygen absorption band and determining the concentration of interstitial oxygen in the body using the measured absorption coefficient.

In another form, the method of the present invention comprises the steps of transmitting an IR beam through a body of crystalline silicon and measuring the absorption coefficient of an interstitial oxygen absorption band at a wavenumber $W_p$ of approximately 1720 cm$^{-1}$. The method further includes the step of determining the concentration of interstitial oxygen in the body using the measured absorption coefficient.

Yet another method according to the invention includes the steps of transmitting an IR beam through a body of crystalline silicon. The body has a thickness, t, exceeding approximately 20 mm and an absorption coefficient at 1107 cm$^{-1}$ exceeding approximately 8/t. The method further includes the steps of measuring the absorption coefficient of an interstitial oxygen absorption band and determining the concentration of interstitial oxygen in the body using the measured absorption coefficient.

A system constructed according to the principles of the present invention may be used for determining interstitial oxygen concentration in a generally cylindrical body of crystalline silicon. The system includes an IR spectrometer for transmitting an IR beam through the body and a crystal positioning device for positioning the body relative to the spectrometer. The spectrometer transmits the IR beam generally transverse to a longitudinal axis of the body and measures the absorption coefficient of an interstitial oxygen absorption band. The system further includes a processor for determining the concentration of interstitial oxygen in the body using the measured absorption coefficient.

Alternatively, the invention may comprise various other methods and systems.

Other objects and features will be in part apparent and in part pointed out hereinafter.

BRIEF DESCRIPTION OF THE DRAWINGS

FIG. 5 is a block diagram of a system according to the preferred embodiment of FIG. 4 including a crystal positioning device.

FIG. 7 illustrates a sample absorbance spectrum according to the preferred embodiment of FIG. 4.

Corresponding reference characters indicate corresponding parts throughout the drawings.

DETAILED DESCRIPTION OF PREFERRED EMBODIMENTS

Figure 1:
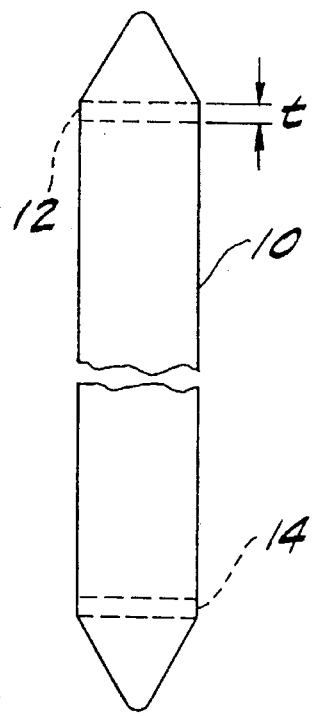
FIG. 1 is a fragmentary view of a crystalline silicon ingot having at least one slug (shown in phantom) cut therefrom according to the prior art.

FIG. 1 is a fragmentary view of a crystalline silicon ingot 10. As described above, IR spectroscopy is widely used for determining interstitial oxygen concentration in silicon. The conventional method for performing spectroscopy on silicon requires cutting a slug 12 (shown in phantom) from the ingot 10. While not necessarily indicated by FIG. 1, the slug 12 is typically cut from an end of ingot 10 and is approximately 2 mm in thickness. Another slug 14 (also shown in phantom) may be cut from ingot 10 at a different axial position. After determining the concentration of interstitial oxygen in slugs 12 and 14, the oxygen concentration at locations between slugs 12 and 14 is then determined by interpolation. In other words, the determination of the oxygen concentration at various axial positions is unavailable by direct measurement without cutting additional slugs similar to slugs 12 and 14 from ingot 10.

Figure 2:
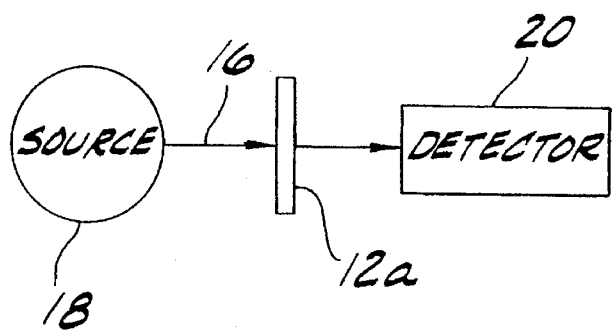
FIG. 2 is block diagram showing infrared spectroscopy of the slug of FIG. 1 according to the prior art.

For purposes of illustration, FIG. 2 shows IR spectroscopy on a slug 12a prepared from slug 12 in accordance with the conventional method. ASTM guidelines require that slug 12 is cut to a thickness of 0.4 to 4 mm and mirror polished on both sides before performing spectroscopy. An IR beam 16 is transmitted from a source 18 through the prepared slug 12a in an axial direction. A detector 20 then detects the portion of the IR beam 16 which is transmitted through prepared slug 12a. Source 18 and detector 20 constitute an IR spectrometer. It is known in the art to perform spectroscopy with a single IR beam or with multiple beams and to include mirrors for directing IR beam 16 through slug 12a and for directing the transmitted portion back to the spectrometer. Detector 20 includes means for processing the detected portion of IR beam 16 to determine the transmittance through slug 12a. Alternatively, absorbance in slug 12a is detected as a function of IR beam 16. A standard IR spectrometer measures either transmittance T, absorbance A or reflectance R, or a combination thereof, where $A=-\log(T)$.

Figure 3A:
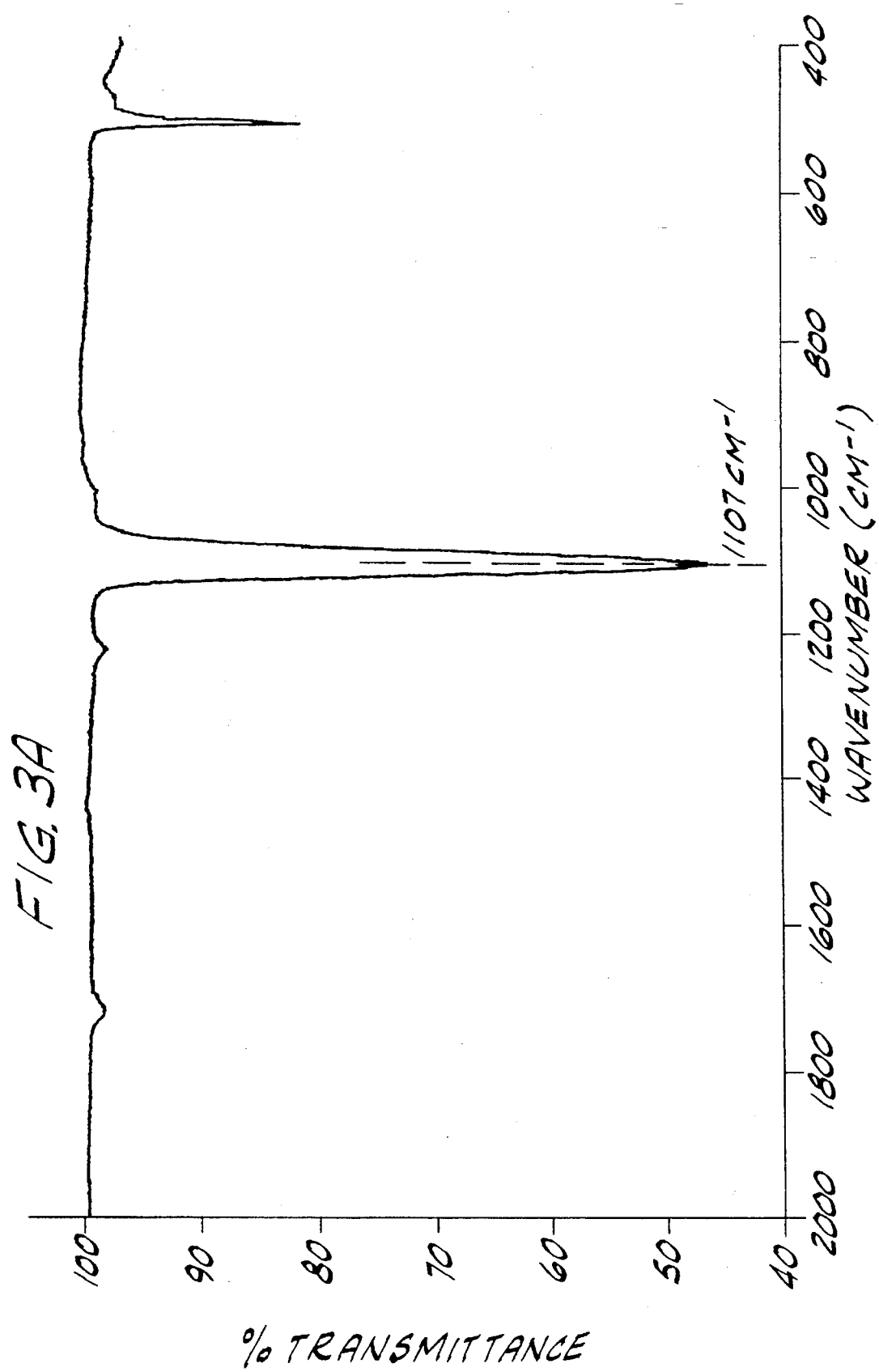
FIGS. 3A and 3B illustrate sample transmittance and absorbance spectrums, respectively, of the slug of FIG. 1 according to the prior art.
Figure 3B:
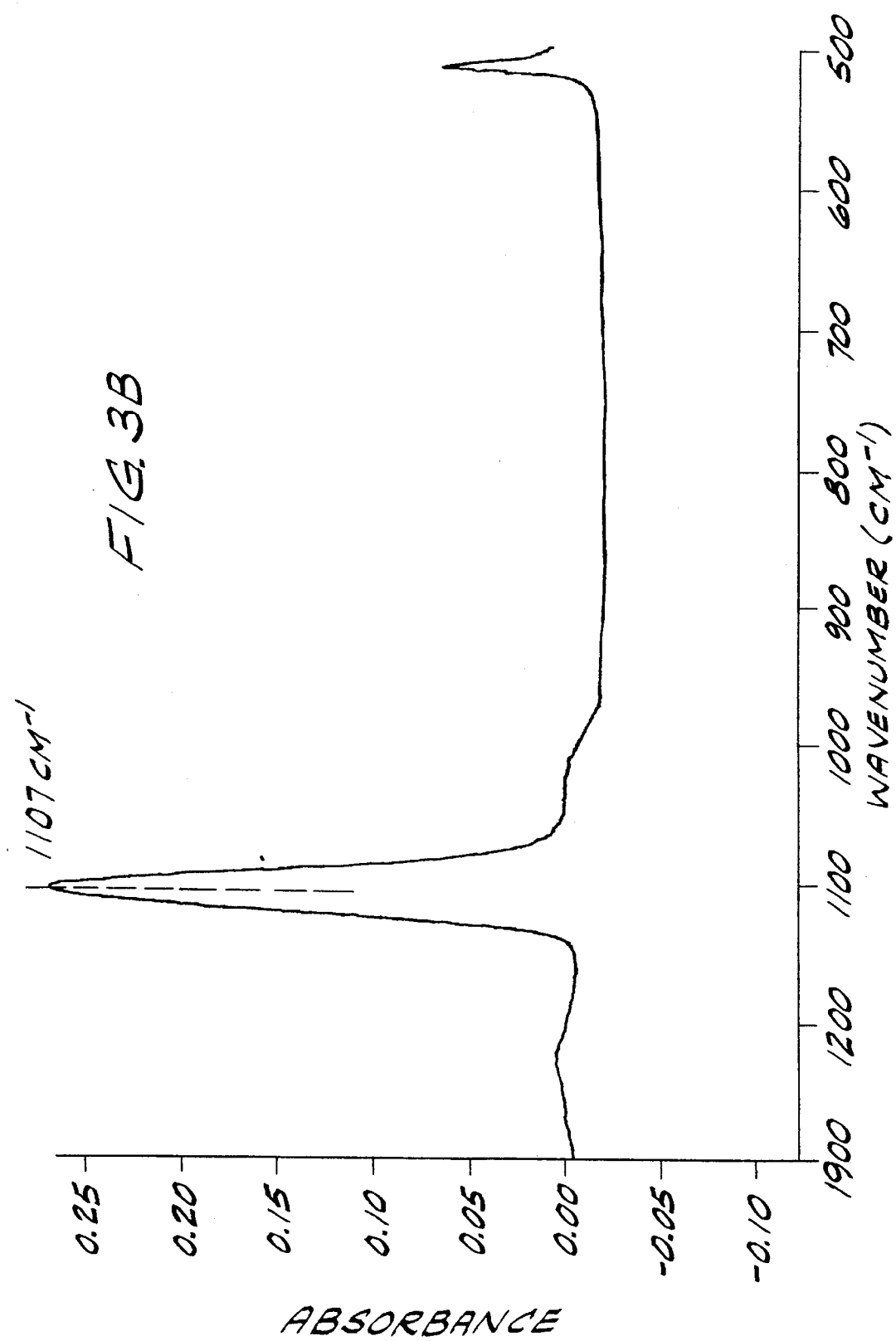

FIG. 3A illustrates a sample transmittance spectrum of slug 12a resulting from spectroscopy performed as shown in FIG. 2. Particularly, FIG. 3A shows the transmittance spectrum for a double-side polished slug which is 2 mm in thickness obtained using a float zone slug of nearly the same thickness as a reference sample. The absorption bands shown in FIG. 3A correspond to the absorption of IR beam 16 by the vibrations of oxygen atoms in the silicon lattice. According to the conventional method, detector 20 measures the transmission spectrum of slug 12a over at least a range of wavenumbers from 900 $cm^{-1}$ to 1300 $cm^{-1}$. Detector 20 further determines an absorption coefficient, $\alpha$, of slug 12a at a wavenumber of about 1107 $cm^{-1}$ as compared to the spectrum of either high-purity silicon or air. Detector 20 then obtains the oxygen concentration from the absorption coefficient by multiplying the absorption coefficient by a standard (e.g., ASTM) conversion factor. Although the 1107 $cm^{-1}$ oxygen absorption band is expected to occur at a wavenumber of 1107 $cm^{-1}$ at room temperature, the exact location of the peak may vary in response to the temperature of slug 12a. Also, slug 12a should have a resistivity, $\rho$, of at least 0.5 $\Omega\cdot cm$ for p-type silicon and 0.05 $\Omega\cdot cm$ for n-type silicon because significant free carrier absorption occurs in crystals having resistivities below these limits which reduces the available energy below that required for satisfactory operation of most spectrometers. In the particular example of FIG. 3A, the concentration of interstitial oxygen, $O_i$, is 23.41 ppma (ASTM F 1188-93). FIG. 3B shows a sample absorbance spectrum corresponding to the transmittance spectrum of FIG. 3A.

As described above, the conventional method requires that spectroscopic measurements are performed on slug 12a which has been prepared in accordance with ASTM guidelines. Slug 12a must have a thickness of 0.4 to 4 mm to obtain a useful absorption spectrum. However, slugs of this size cannot be manufactured into wafers in a cost effective manner. Thus, expensive silicon is wasted by the conventional method. Further, ASTM guidelines require that slug 12 be cut and mirror polished on both sides before performing spectroscopy to reduce variable reflections of IR beam 16 at the surfaces of slug 12a, although it is common in the industry to merely cut and grind slug 12 without polishing. In either case, the preparation of slugs 12 and 14 wastes valuable time and delays the response time for modifying the growing process for controlling oxygen content in subsequently grown crystals.

Figure 4:
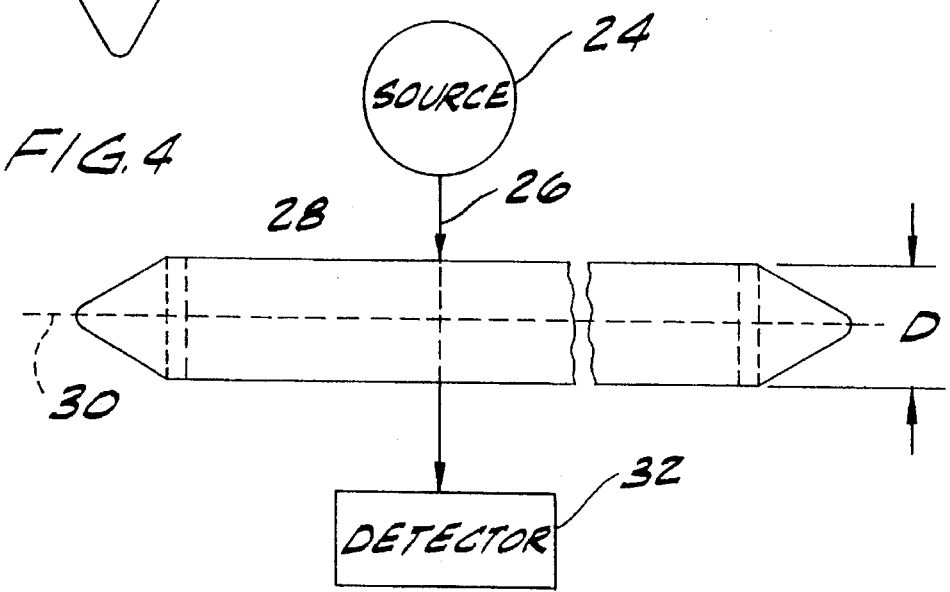
FIG. 4 is a block diagram showing infrared spectroscopy of a silicon crystal ingot according to a preferred embodiment of the present invention.

As shown in FIG. 4, spectroscopy performed according to the present invention employs a source 24 transmitting an IR beam 26 through a generally cylindrical crystal 28. The crystal 28 constitutes a body of crystalline silicon and is preferably an ingot of crystalline silicon having a longitudinal axis 30 and a diameter D. The source 24 transmits the IR beam 26 through crystal 28 generally transverse to the axis 30. It should be understood that an as-grown crystal, such as crystal 28, may not have a uniform diameter, although it is generally cylindrical. For this reason, diameter D may vary slightly at different axial positions along axis 30.

In a preferred embodiment of the invention, a detector 32 detects the portion of IR beam 26 transmitted through crystal 28. Preferably, the detector 32 includes a processor (not shown) for performing the calculations necessary to measure an absorption spectrum of crystal 28. Due to the thickness of material of crystal 28 through which IR beam 26 is transmitted, however, the absorption band at the 1107 $cm^{-1}$ wavenumber is too large to provide useful information regarding the absorption of IR beam 26 by crystal 28. FIG. 7 shows a sample absorption spectrum according to a preferred embodiment of the invention. Note that below approximately 1500 $cm^{-1}$, the IR beam 26 is completely absorbed. However, there is a well-defined absorption band at approximately 1720 $cm^{-1}$.

The existence of an interstitial oxygen absorption band at 1720 $cm^{-1}$ is known from "Practical Fourier Transform infrared Spectroscopy," edited by J. R. Ferraro and K. Krishnan, Academic Press, 1990. The intensity of the 1720 $cm^{-1}$ absorption band, however, is approximately only 1.6% of the intensity of the 1107 $cm^{-1}$ band. Although the existence of the 1720 $cm^{-1}$ band is known, a quantitative analysis of interstitial oxygen using this band has not been possible or necessary until the present invention due to the small intensity of this band relative to the background or baseline spectrum as measured for slugs such as slugs 12 and 14. Thus, the determination of interstitial oxygen concentrations using the conventional method based on the 1720 band provides measurements which are too inaccurate for IC device manufacturing. On the other hand, this invention describes a method whereby accurate measurements of the interstitial oxygen concentration can be obtained using the 1720 cm$^{-1}$ band. Furthermore, these measurements are possible on very thick samples, for which the conventional method fails.

In operation, source 24 transmits IR beam 26 through crystal 28 generally transverse to longitudinal axis 30. Preferably, crystal 28 has a diameter D of at least 75 mm. Detector 32 measures the IR absorption spectrum of crystal 28 over a range of wavenumbers from approximately 1500 cm$^{-1}$ to approximately 1900 cm$^{-1}$. Endpoints are defined at either side of the 1720 absorption band and a baseline spectrum is defined by essentially drawing a straight line between the endpoints. An absorption peak (corresponding to a minimum transmittance) occurs at a wavenumber of approximately 1720 cm$^{-1}$ at room temperature. However, it is to be understood that the location of this interstitial oxygen band may vary as a function of the temperature of crystal 28. The processor of detector 32 also measures the transmittance of the baseline at 1720 cm$^{-1}$ and measures the peak absorption at 1720 cm$^{-1}$ from the IR absorption spectrum, i.e., the difference between the baseline and minimum transmittances. In a similar manner, the absorption coefficient can be obtained in terms of absorbance rather than transmittance due to the relationship between the two parameters. The absorption coefficient is determined from the peak absorption and a measurement of the path length of the IR beam 26. Further, the processor of detector 32 determines the concentration of interstitial oxygen in crystal 28 as a function of the band at 1720 cm$^{-1}$ by multiplying the determined absorption coefficient by a conversion factor of approximately 390 ppma·cm or approximately $2 \times 10^{19}$ atoms/cm$^2$. This conversion factor is consistent with the conversion factor recommended by ASTM F 1188-93. Therefore, this conversion factor may vary depending on ASTM guidelines accepted in the industry at the time. In a preferred embodiment, the standard ASTM conversion factor (ASTM F 1188-93) is of the order of 1.6% of the conversion factor used in this measurement because the intensity of the 1720 wavenumber absorption band is approximately 1.6% of the intensity of the 1107 band. Improved accuracy and precision may be obtained by allowing for a nonlinear baseline and using integrated peak intensity rather than peak height to determine the absorption coefficient. Preferably, such a determination is performed with an FTIR spectroscope.

According to the present invention, spectroscopy as illustrated in FIG. 4 is possible for an as-grown ingot, such as crystal 28, as soon as crystal 28 cools. That is, preparation of the surface is no longer required. However, it should be noted that the method of the present invention can be performed on a prepared, i.e., cut and polished, surface. Although an as-grown crystal typically does not have a uniform diameter, its surface is essentially smooth at the points of entry and exit of IR beam 26. An external measurement of diameter D, corresponding to the length of the path of IR beam 26 through crystal 28 can be taken with calipers. Alternatively, crystal 28 is first ground to a known uniform diameter. Thus, the present invention eliminates wasted time and provides improved response time for controlling the concentration of interstitial oxygen in crystalline silicon.

In a preferred embodiment, crystal 28 is grown in accordance with the Czochralski method in which a seed crystal (not shown) is introduced to a melt of silicon contained in a silica crucible (not shown). The seed crystal is slowly withdrawn from the melt, in an inert atmosphere such as argon and the silicon solidifies on the seed to produce the growth of a crystal rod. Commonly assigned U.S. Pat. No. 4,436,577, the entire disclosure of which is incorporated herein by reference, describes a method of regulating concentration and distribution of oxygen in Czochralski grow silicon. This patent discloses varying the rates at which the crystal and the crucible are rotated as the crystal is drawn from the melt for achieving regulation of the distribution of the oxygen content in the crystal. Since a determination of the concentration of oxygen in crystal 28 is available without the delay associated with preparing slugs 12 and 14, the method of this patent may be more efficiently performed.

FIG. 5 illustrates a system 34 for performing spectroscopy by the method shown in FIG. 4. As shown, the system 34 includes a spectrometer 36 comprised of source 24 and detector 32. Preferably, the spectrometer 36 is an FTIR spectrometer. Source 24 transmits IR beam 26 through crystal 28 in a plane 38 which is generally transverse to axis 30. In a preferred embodiment, crystal 28 is mounted on a rail table 40 constituting a linear positioning device. Preferably, the rail table 40 has a threaded screw-drive mechanism 42 and at least one rail 43 extending the length of rail table 40. Rail table 40 also includes a traveler 44. The traveler 44 is mounted on the screw-drive mechanism 42 and has a threaded portion (not shown) mated with the threaded screw-drive mechanism 42. In this embodiment, a stepper motor 46 incrementally rotates threaded screw-drive mechanism 42 for moving traveler 46 in a linear direction along the rail 43 of rail table 40.

A clamp assembly 48 is mounted on traveler 44 including a pair of U-shaped clamps 50 and 52. The clamps 50 and 52 have a radius of curvature slightly larger than the radius of crystal 28 and securely hold crystal 28 in position on the clamping assembly 48. Preferably, clamping assembly 48 has sufficient strength and rigidity for supporting the weight of an as-grown ingot of crystalline silicon. Further, clamps 50 and 52 can be exchanged for larger or smaller clamps for securing crystals having larger or smaller diameters, respectively. Preferably, a measuring device such as calipers (not shown) is mounted on traveler 44 for measuring the diameter of crystal 28 at the points of entry and exit of IR beam 26.

In a preferred embodiment, a computer 54 controls operation of rail table 40 for re-positioning crystal 28 to obtain additional data points. Spectrometer 36 re-transmits IR beam 26 at various axial positions along longitudinal axis 30 of crystal 28 as crystal 28 is moved by traveler 44. In this manner, spectrometer 36 obtains a complete analysis of the distribution of oxygen throughout the entirety of crystal 28 without cutting additional slugs and, thus, without wasting valuable material and time. Alternatively, computer 54 is also operably connected to spectrometer 36 for performing the calculations necessary for determining interstitial oxygen concentration in crystal 28 or for aiding detector 32 in performing the calculations.

Rail table 40 is of the type manufactured by Daedal Positioning Systems and Controls and can be operated in either a horizontal or vertical direction. Custom widths up to 32 inches and travel lengths to 10 feet are available from this manufacturer. Preferably, rail table 40 is sized to position silicon ingots as long as 1.5 meters and 200 mm in diameter. It is to be understood, however, that rail table 40 can be modified to have a longer travel for accommodating longer crystals and that clamps 50 and 52 can be modified for accommodating larger crystals.

Figure 6:
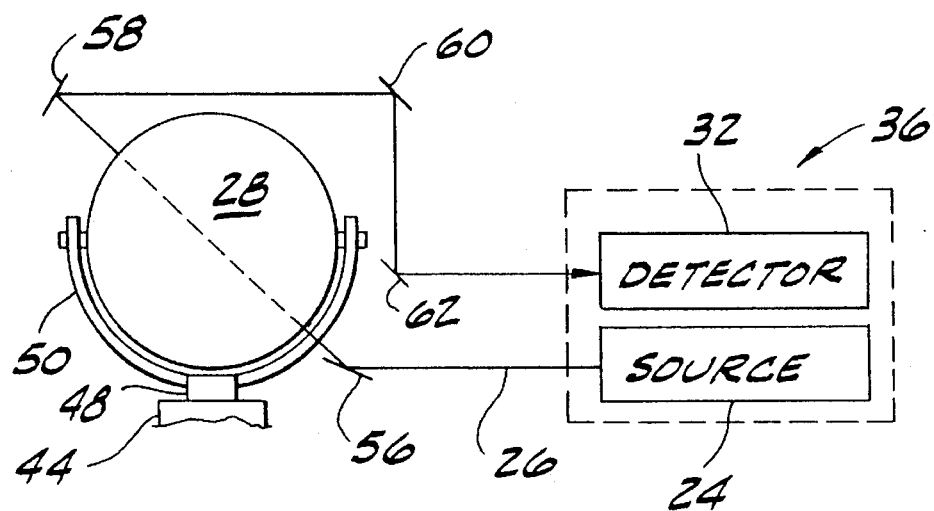
FIG. 6 shows the system of FIG. 5 in greater detail.

Referring to FIG. 6, crystal 28 is shown in cross-section and positioned relative to spectrometer 36 according to the embodiment of the invention illustrated in FIGS. 4 and 5. As shown, spectrometer 36 comprises source 24 and detector 32. Source 24 transmits IR beam 26 through a diameter of crystal 28 and detector 32 detects the portion of the IR beam 26 transmitted through crystal 28. As further shown, spectrometer 36 includes a number of mirrors 56, 58, 60 and 62 for directing IR beam 26 from source 24 through crystal 28 and back to detector 32.

FIG. 7 illustrates a sample IR absorbance spectrum measured through the diameter of a 200 mm ingot ($O_i \approx 19.2$ ppma (ASTM F 1188-93), $\rho \approx 12$ Ω·cm, n-type) in accordance with the present invention. As shown, the absorbance at 1107 cm$^{-1}$ is too large for measuring the absorption coefficient. In other words, the transmittance of the sample at this wavenumber is below the detection limit of a spectrometer. In a preferred embodiment of the invention, the signal-to-noise ratio of spectrometer 36 is maximized by, for example, increasing the intensity of IR beam 26 from source 24. By maximizing the signal-to-noise ratio, detector 32 (or computer 54) is able to develop an ingot interstitial oxygen measurement based on the absorption band at 1720 cm$^{-1}$ for crystals having a resistivity as low as 0.5 Ω·cm for p-type silicon and 0.05 Ω·cm for n-type silicon. Also, an analysis of the peak height and background absorbance in a typical spectrum like that shown in FIG. 7 leads to the conclusion that the method of the present invention performs acceptably for samples having a crystal diameter up to approximately 700 mm. This method is applicable to smaller crystal diameters as well.

Figure 8:
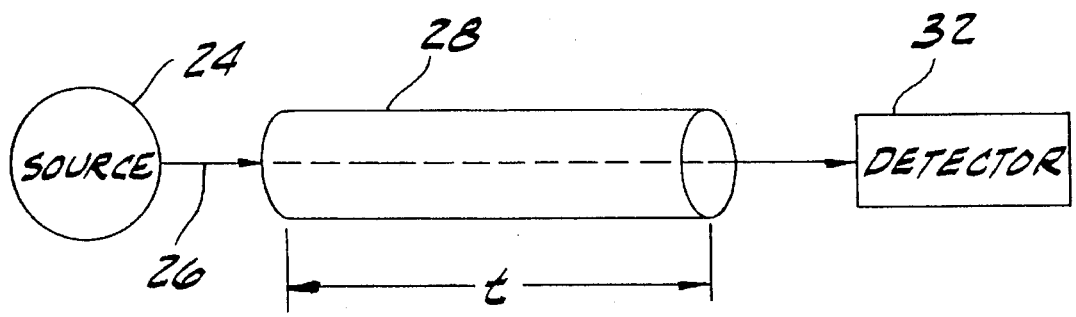
FIG. 8 is a block diagram showing infrared spectroscopy of a body of crystalline silicon according to another preferred embodiment of the present invention.

FIG. 8 illustrates another embodiment of the present invention in which crystal 28 is oriented so that source 24 transmits IR beam 26 through crystal 28 in an axial direction. Preferably, crystal 28 has a thickness, t, of at least 20 mm and the absorption coefficient is at least 8/t at 1107 cm$^{-1}$. Under such conditions the measurement of the 1107 cm$^{-1}$ absorption band would not be possible with conventional spectrometers.

EXAMPLES

Unless otherwise indicated, each of the concentrations of interstitial oxygen in the following examples is determined using a conversion factor (i.e., 390 ppma·cm) consistent with the conversion factor recommended by ASTM F 1188-93.

1. IR spectroscopy of a phosphorous-doped silicon crystal (D≈207 mm, $\rho \approx 12$ Ω·cm) was performed according to the embodiment of the invention shown in FIG. 4. The surface of the crystal was in the as-grown condition (relatively smooth). The absorption coefficient at the 1720 cm$^{-1}$ band was determined to be $\alpha_{1720}$=0.053 cm$^{-1}$. Multiplying by a conversion factor of 390 ppma·cm yields an interstitial oxygen concentration of $O_i$=20.6 ppma.

2. IR spectroscopy of a boron-doped silicon crystal (D=200 mm, $\rho \approx 10$ Ω·cm) was performed according to the embodiment of the invention shown in FIG. 4. The surface of the crystal was ground to a uniform diameter of 200 mm. The absorption coefficient at the 1720 cm$^{-1}$ band was determined to be $\alpha_{1720}$=0.0464 cm$^{-1}$. Multiplying by a conversion factor of 390 ppma·cm yields an interstitial oxygen concentration of $O_i$=18.1 ppma.

3. IR spectroscopy of a phosphorous-doped silicon crystal (D≈207 mm, $\rho \approx 0.4$ Ω·cm) was performed according to the embodiment of the invention shown in FIG. 4. The surface of the crystal was in the as-grown condition (relatively smooth). The absorption coefficient at the 1720 cm$^{-1}$ band was determined to be $\alpha_{1720}$=0.0458 cm$^{-1}$. Multiplying by a conversion factor of 390 ppma·cm yields an interstitial oxygen concentration of $O_i$=17.9 ppma.

4. IR spectroscopy of a boron-doped silicon crystal (D≈154 mm, $\rho \approx 12$ Ω·cm) was performed according to the embodiment of the invention shown in FIG. 4. The surface of the crystal was in the as-grown condition (relatively smooth). The absorption coefficient at the 1720 cm$^{-1}$ band was determined to be $\alpha_{1720}$=0.061 cm$^{-1}$. Multiplying by a conversion factor of 390 ppma·cm yields an interstitial oxygen concentration of $O_i$=23.8 ppma.

5. IR spectroscopy of a boron-doped silicon crystal (D≈154 mm, $\rho \approx 12$ Ω·cm) was performed according to the embodiment of the invention shown in FIG. 8. The length of the crystal was 14.5 cm. The absorption coefficient at the 1720 cm$^{-1}$ band was determined to be $\alpha_{1720}$=0.0524 cm$^{-1}$. Multiplying by a conversion factor of 390 ppma·cm yields an interstitial oxygen concentration of $O_i$=20.4 ppma.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A nondestructive method for determining a concentration of interstitial oxygen in an ingot of crystalline silicon, said ingot being generally cylindrical and having a longitudinal axis along which the ingot was grown, said method comprising the steps of:

transmitting an infrared (IR) beam through the ingot in a direction generally transverse to the longitudinal axis of the ingot;

measuring the absorption coefficient of the transmitted IR beam with respect to an interstitial oxygen absorption band; and determining the concentration of interstitial oxygen in the ingot as a function of the measured absorption coefficient.

2. The method of claim 1 wherein the step of measuring the absorption coefficient comprises the steps of determining a minimum transmittance at a wavenumber $W_p$, defining a baseline over a range of wavenumbers including the wavenumber $W_p$ and determining a baseline transmittance at the wavenumber $W_p$ wherein the measured absorption coefficient is a function of the minimum and baseline transmittances.

3. The method of claim 2 wherein the wavenumber $W_p$ is approximately 1720 cm$^{-1}$.

4. The method of claim 2 wherein the range of wavenumbers is from approximately 1500 cm$^{-1}$ to approximately 1900 cm$^{-1}$.

5. The method of claim 1 wherein the step of transmitting the IR beam comprises transmitting the IR beam generally through a diameter of the ingot.

6. The method of claim 5 wherein the diameter of the ingot exceeds approximately 75 mm.

7. The method of claim 1 wherein the step of determining the concentration of interstitial oxygen in the ingot comprises the step of multiplying the measured absorption coefficient by a conversion factor to convert the measured absorption coefficient to ppma or atoms/cm$^3$.

8. The method of claim 1 wherein the ingot has a thickness, t, exceeding approximately 20 mm and an absorption coefficient at approximately 1107 cm$^{-1}$ exceeding approximately 8/t.

9. The method of claim 1 wherein the step of measuring the absorption coefficient comprises the steps of determining a maximum absorbance at a wavenumber $W_p$, defining a baseline over a range of wavenumbers including the wavenumber $W_p$ and determining a baseline absorbance at the wavenumber $W_p$ wherein the measured absorption coefficient is a function of the maximum and baseline absorbances.

10. The method of claim 9 wherein the wavenumber $W_p$ is approximately 1720 cm$^{-1}$.

11. A nondestructive method for determining a concentration of interstitial oxygen in an ingot of crystalline silicon, said ingot being generally cylindrical and having a longitudinal axis along which the ingot was grown, said method comprising the steps of:

transmitting an infrared (IR) beam through a first portion of the ingot in a direction generally transverse to the longitudinal axis of the ingot;

measuring the absorption coefficient of the transmitted IR beam with respect to an interstitial oxygen absorption band of the first portion of the ingot;

determining the concentration of interstitial oxygen in the first portion of the ingot as a function of the measured absorption coefficient of the first portion of the ingot;

re-transmitting the IR beam through a second portion of the ingot in a direction generally transverse to the longitudinal axis of the ingot;

measuring the absorption coefficient of the transmitted IR beam with respect to an interstitial oxygen absorption band of the second portion of the ingot; and determining the concentration of interstitial oxygen in the second portion of the ingot as a function of the measured absorption coefficient of the second portion of the ingot.

12. A system for determining a concentration of interstitial oxygen in an ingot of crystalline silicon, said ingot being generally cylindrical and having a longitudinal axis along which the ingot was grown, said system comprising:

an infrared (IR) spectrometer for transmitting an IR beam through the ingot;

a positioning device for positioning the ingot relative to the spectrometer such that the spectrometer transmits the IR beam through the ingot in a direction generally transverse to the longitudinal axis of the ingot, the spectrometer measuring the absorption coefficient of the transmitted IR beam with respect to an interstitial oxygen absorption band; and a processor for determining the concentration of interstitial oxygen in the ingot as a function of the measured absorption coefficient.

\* \* \* \* \*